(12) United States Patent
Bauer

(10) Patent No.: US 6,503,701 B1
(45) Date of Patent: *Jan. 7, 2003

(54) ANALYTIC SENSOR APPARATUS AND METHOD

(75) Inventor: Alan Joseph Bauer, Jerusalem (IL)

(73) Assignee: Biosensor Systems Design, Inc., Cedarhurst, NY (US)

( * ) Notice: Subject to any disclaimer, the term of this patent is extended or adjusted under 35 U.S.C. 154(b) by 262 days.

This patent is subject to a terminal disclaimer.

(21) Appl. No.: 09/979,354

(22) PCT Filed: Jun. 5, 2000

(86) PCT No.: PCT/US00/15400

§ 371 (c)(1),
(2), (4) Date: Nov. 21, 2001

(87) PCT Pub. No.: WO00/77522

PCT Pub. Date: Dec. 21, 2000

(30) Foreign Application Priority Data

| Jun. 15, 1999 | (IL) | 130478 |
| Aug. 1, 1999 | (IL) | 131193 |
| Sep. 21, 1999 | (IL) | 131983 |
| Sep. 21, 1999 | (IL) | 132491 |
| Nov. 22, 1999 | (IL) | 133059 |
| Dec. 6, 1999 | (IL) | 133323 |

(51) Int. Cl.[7] .................. C12Q 1/00; C12M 1/34; C12M 1/00
(52) U.S. Cl. ............ 435/4; 435/287.1; 435/289.1; 435/283.1
(58) Field of Search ............... 435/4, 287.1, 289.1, 435/283.1

(56) References Cited

U.S. PATENT DOCUMENTS

| 4,822,566 A | 4/1989 | Newman | 422/68 |
| 4,839,017 A | 6/1989 | Taniguchi et al. | 435/291 |
| 4,916,075 A | 4/1990 | Malmros et al. | 435/291 |
| 5,156,810 A | 10/1992 | Ribi et al. | 422/82.01 |
| 5,264,103 A | 11/1993 | Yoshioka et al. | 204/403 |
| 5,482,855 A | 1/1996 | Hayashi et al. | 435/287.1 |

(List continued on next page.)

FOREIGN PATENT DOCUMENTS

| EP | 441 120 | 8/1991 |
| WO | WO 97 01092 | 1/1997 |
| WO | WO 97 22875 | 6/1997 |
| WO | WO 97 414125 | 11/1997 |
| WO | WO 98 10289 | 3/1998 |

OTHER PUBLICATIONS

Radmacher, Manfred et al., *Direct Observation of Enzyme Activity with the Atomic Force Microscope*. Science 265:1577, Sep. 9, 1994.

(List continued on next page.)

Primary Examiner—Louise N. Leary
(74) Attorney, Agent, or Firm—Arthur S. Bickel

(57) ABSTRACT

A sensor for detecting analytes of interest is described. Analyte presence or concentration is determined through measurement of changes in induced electromotive force, current or other electrical property in a sensor strip during analyte exposure to the sensor. According to one class of embodiments, the present device immobilizes natural or synthetic macromolecules sufficiently close to an electrically-conductive base member to insure that interaction of analyte with the macromolecules will lead to altered de novo electrical signals in the sensor strip of base member and macromolecules. Performance of the sensor is enhanced by the use of resistance-modifying element in a circuit that includes the sensor strip, and by an adhesive agent disposed between the base member and at least one electrical lead of a detection unit.

27 Claims, 10 Drawing Sheets

U.S. PATENT DOCUMENTS

| | | | |
|---|---|---|---|
| 5,491,097 A | 2/1996 | Ribi et al. | 436/518 |
| 5,543,326 A | 8/1996 | Heller et al. | 436/817 |
| 5,585,646 A | 12/1996 | Kossovsky et al. | 257/40 |
| 5,605,662 A | 2/1997 | Tu et al. | 435/7.1 |
| 5,620,854 A | 4/1997 | Holzrichter et al. | 435/6 |
| 5,719,033 A | 2/1998 | Ackley et al. | 435/7.92 |
| 5,783,056 A | 7/1998 | Hampp et al. | 204/403 |
| 6,342,347 B1 * | 1/2002 | Bauer | 435/4 |

OTHER PUBLICATIONS

Patel et al., *Immobilization of Protein Molecules onto Homogeneous and Mixed Carboxylate–Terminated Self–Assembled Monolayers*. Langmuir 6485–6490, 1997.

Barda, Amos et al., *NAD+ Dependent Enzyme Electrodes: Electrical Contact Cofactor–Dependent Enzymes and Electrodes*. J. Am. Chem Soc. 119:9114–91119, 1997.

Souteyrand E. et. Al., Direct Detection of Biomolecules by Electrochemical Impedance Measurements. Sensors and Actuators B. vol. B20, No. 1. May 1, 1994. pp. 63–69; abstract, figures 1, 2.

Wilner, Itamar et al., *Assembly of Functionalized Monolayers of Redox Proteins on Electrode Surfaces: Novel Bioelectronic and Optobioelectronic Systems*. Biosensors & Bioelectronics 12, No. 4, pp. 337–356, 1997.

* cited by examiner

ANALYTIC SENSOR APPARATUS AND METHOD

BACKGROUND OF THE INVENTION

1. Field of the Invention

This invention pertains to a sensor and method for detecting or quantifying analytes. More particularly the present invention is directed to the detection of analytes by interaction thereof with an immobilized macromolecular entity and the analysis of certain de novo electrical effects that are produced as a result of such interactions. The invention is an extension of the sensor and method described in PCT application PCT/IL99/00309 of common assignee herewith.

2. Description of the Related Art

Chemical and biological sensors are devices that can detect or quantify analytes by virtue of interactions between targeted analytes and macromolecular binding agents such as enzymes, receptors, DNA strands, heavy metal chelators, or antibodies. Such sensors have practical applications in many areas of human endeavor. For example, biological and chemical sensors have potential utility in fields as diverse as blood glucose monitoring for diabetics, detection of pathogens commonly associated with spoiled or contaminated food, genetic screening, and environmental testing.

Chemical and biological sensors are commonly categorized according to two features, namely, the type of material utilized as binding agent and the means for detecting an interaction between binding agent and targeted analyte or analytes. Major classes of biosensors include enzyme (or catalytic) biosensors, immunosensors and DNA biosensors. Chemical sensors make use of synthetic macromolecules for detection of target analytes. Some common methods of detection are based on electron transfer, generation of chromophores or fluorophores, changes in optical or acoustical properties, or alterations in electric properties when an electrical signal is applied to the sensing system.

Enzyme (or catalytic) biosensors utilize one or more enzyme types as the macromolecular binding agents and take advantage of the complementary shape of the selected enzyme and the targeted analyte. Enzymes are proteins that perform most of the catalytic work in biological systems and are known for highly specific catalysis. The shape and reactivity of a given enzyme limit its catalytic activity to a very small number of possible substrates. Enzymes are also known for speed, working at rates as high as 10,000 conversions per second per enzyme molecule. Enzyme biosensors rely on the specific chemical changes related to the enzyme/analyte interaction as the means for determining the presence of the targeted analyte. For example, upon interaction with an analyte, an enzyme may generate electrons, a colored chromophore or a change in pH (due to release of protons) as the result of the relevant catalytic enzymatic reaction. Alternatively, upon interaction with an analyte, an enzyme may cause a change in a fluorescent or chemiluminescent signal that can be recorded by an appropriate detection system.

Immunosensors utilize antibodies as binding agents. Antibodies are protein molecules that bind with specific foreign entities, called antigens, that can be associated with disease states. Antibodies attach to antigens and either remove the antigens from a host and/or trigger an immune response. Antibodies are quite specific in their interactions and, unlike enzymes, they are capable of recognizing and selectively binding to very large bodies such as single cells. Thus, antibody-based biosensors allow for the identification of certain pathogens such as dangerous bacterial strains. As antibodies generally do not perform catalytic reactions, there is a need for special methods to record the moment of interaction between target analyte and recognition agent antibody. Changes in mass (surface plasmon resonance, acoustic sensing) are often recorded; other systems rely on fluorescent probes that give signals responsive to interaction between antibody and antigen. Alternatively, an enzyme bound to an antibody can be used to deliver the signal through the generation of color or electrons; the ELISA (Enzyme-Linked ImmunoSorbent Assay) is based on such a methodology.

DNA biosensors utilize the complimentary nature of the nucleic acid double-stands and are designed for the detection of DNA or RNA sequences usually associated with certain bacteria, viruses or given medical conditions. A sensor generally uses single-stands from a DNA double helix as the binding agent. The nucleic acid material in a given test sample is then denatured and exposed to the binding agent. If the strands in the test sample are complementary to the strands used as binding agent, the two interact. The interaction can be monitored by various means such as a change in mass at the sensor surface or the presence of a fluorescent or radioactive signal. Alternative arrangements have binding of the sample of interest to the sensor and subsequent treatment with labeled nucleic acid probes to allow for identification of the sequence(s) of interest.

Chemical sensors make use of non-biological macromolecules as binding agents. The binding agents show specificity to targeted analytes by virtue of the appropriate chemical functionalities in the macromolecules themselves. Typical applications include gas monitoring or heavy metal detection; the binding of analyte may change the conductivity of the sensor surface or lead to changes in charge that can be recorded by an appropriate field-effect transistor (FET). Several synthetic macromolecules have been used successfully for the selective chelation of heavy metals such as lead.

The present invention has applicability to all of the above noted binding agent classes.

Known methods of detecting interaction of analyte and binding agent can be grouped into several general categories: chemical, optical, acoustical, and electrical. In the last, a voltage or current is applied to the sensor surface or an associated medium. As binding events occur on the sensor surface, there are changes in electrical properties of the system. The leaving signal is altered as function of analyte presence.

The most relevant prior art to the present invention involves sensors that are based on electrical means for analyte detection. There are several classes of sensors that make use of applied electrical signals for determination of analyte presence. "Amperometric" sensors make use of oxidation-reduction chemistries in which electrons or electrochemically active species are generated or transferred due to analyte presence. An enzyme that interacts with an analyte may produce electrons that are delivered to an appropriate electrode; alternatively, an amperometric sensor may employ two or more enzyme species, one interacting with analyte, while the other generates electrons as a function of the action of the first enzyme (a "coupled" enzyme system). Glucose oxidase has been used frequently in amperometric biosensors for glucose quantification for diabetics. Other amperometric sensors make use of electrochemically active species whose presence alters the system applied voltage as recorded at a given sensor electrode. Not all sensing systems can be adapted for electron generation or transfer, and thus many sensing needs cannot be met by amperometric methods alone. The general amperometric method makes use of an applied voltage and effects of electrochemically active species on said voltage. An example of an amperometric sensor is described in U.S. Pat. No. 5,593,852, in which Heller and Pishko disclose a glucose sensor that relies on electron transfer effected by a redox enzyme and electrochemically-active enzyme cofactor species. The present invention does not require application of an eternal voltage, oxidation/reduction chemistry, or electron generation/transfer.

An additional class of electrical sensing systems includes those sensors that make use primarily of changes in an electrical response of the sensor as a function of analyte presence. Some systems pass an electric current through a given medium; if analyte is present, there is a corresponding change in exit electrical signal, and this change implies that analyte is present. In some cases, the binding agent-analyte complex causes an altered signal, while in other systems, the bound analyte itself is the source of changed electrical response. Such sensors are distinguished from amperometric devices in that they do not necessarily require the transfer of electrons to an active electrode. Sensors based on the application of an electrical signal are not universal, in that they depend on alteration of voltage or current as a function of analyte presence; not all sensing systems can meet such a requirement. An example of this class of sensors is U.S. Pat. No. 5,698,089, in which Lewis and Freund disclose a chemical sensor in which analyte detection is determined by change of an applied electrical signal. Binding of analyte to chemical moieties arranged in an array alters the conductivity of the array points; unique analytes can be determined by the overall changes in conductivity of all of the array points. The present invention does not rely on arrays or changes of applied electrical signal as a function of analyte presence. The present sensor does not require any applied electrical or electromagnetic signal.

Several other publications that do not fall into the preceding categories are worthy of mention in the prior art. Radmacher, et al. (*Science* 265:1577–1579 (1994)) noted the existence of augmented spatial fluctuations in enzymes interacting with substrates, but did not apply this phenomenon to analyte detection. Holzrichter, et al., U.S. Pat. No. 5,620,854, did make use of macromolecule motion to detect analyte; their system relies specifically on atomic force or scanning tunneling microscopes for detection of said motion. An additional patent is that of Stanbro, et al., U.S. Pat. No. 5,114,674, which discloses a sensor that is based on the interference of applied electrical fields. Interaction of target analyte with a binding agent alters the interference of the applied electrical field. The present invention does not make use of applied electrical fields, currents, or voltages.

Other prior-art voltage-based sensors require the use of semiconducting field-effect transistors (FET's) and rely on the chemical generation or physical trapping of charged species near the sensor surface. The method has found widespread use in the detection of positively-charged heavy metals as well as analytes that are involved in proton ($H^+$) generating enzyme reactions. Sato, et al. ("Endoscopic Urease Sensor System for Detecting *Helicobacter pylori* on Gastric Mucosa", *Gastrointestinal Endoscopy* 49: 32–38 (1999)) describe a pH-sensitive FET for the detection of the enzyme urease associated with the pathogenic bacteria *H pylori*. The present invention does not rely on the use of a FET in the sensor element contacted to analyte-containing samples.

While hundreds of sensors have been described in patents and in the scientific literature, actual commercial use of such sensors remains limited. In particular, virtually all sensor designs set forth in the prior art contain one or more inherent weaknesses. Some lack the sensitivity and/or speed of detection necessary to accomplish certain tasks. Other sensors lack long-term stability. Still others cannot be sufficiently miniaturized to be commercially viable or are prohibitively expensive to produce. Some sensors must be pre-treated with salts and/or enzyme cofactors, a practice that is inefficient and bothersome. To date, virtually all sensors are limited by the known methods of determining that contact has o between an immobilized binding agent and targeted analytes. Use of fluorescent or other external detection probes adds to sensor production requirements and reduces lifetimes of such sensor systems. Additionally, the inventor believes that there is no sensor method disclosed in the prior art that is general applicable to the vast majority of macromolecular binding agents, including enzymes, antibodies, antigens, nucleic acids, receptors, and synthetic binding agents.

SUMMARY OF THE INVENTION

It is therefore a primary object of the present invention to provide an improved analyte detection system, in which a detection unit is electrically connected to a sensor strip so as to allow for detection of internally-generated electrical signals in the sensor strip that are responsive to analyte presence;

It is a further object of the invention to describe an electrical circuit that includes sensor strip and detection unit to allow for rapid, sensitive, and inexpensive analyte detection; and, It is an additional object of the invention to improve the consistency and ease of use in detection of an analyte in a sensor system by inclusion of resistance-modifying elements in the detector unit-sensor strip electrical circuit.

These and other objects of the present invention are attained by a sensor that includes a base member having a conductive electrical property; a macromolecular entity bound to the base member, wherein the macromolecular entity and the base member define a sensor strip, the macromolecular entity being interactive at a level of specificity with a predetermined analyte, and an electrical signal is internally-generated in the sensor strip responsive to presence of the analyte; and, a resistance-modifying element disposed in a circuit between the base member and a detection unit for detection of the electrical signal.

According to still another aspect of the invention, the resistance-modifying element is a self-assembled monolayer.

According to yet another aspect of the invention, the resistance-modifying element is a chemical entity.

According to another aspect of the invention, the internally-generated electrical signal is further processed for determination of analyte presence or concentration.

According to yet another aspect of the invention, a serial dilution unit is included for the determination of analyte concentration.

The invention provides a method for detecting analyte, including the following steps: providing an electrically conductive base member; immobilizing at least one macromolecule in proximity to the base member, wherein the macromolecule is capable of interacting at a level of specificity with a predetermined analyte, wherein the base member and the macromolecule define a sensor strip; exposing predetermined analyte to the macromolecule; and, detecting an electrical signal internally-generated in the sensor strip, the electrical signal being responsive to a presence of the predetermined analyte, wherein the step of detecting is performed with an electrical circuit that includes the base member and a resistance modifying element.

According to an aspect of the invention, contact between equipotential electrodes of a detection unit and the sensor strip is facilitated by presence of an adhesive agent between the sensor strip and detection unit electrodes.

According to an additional aspect of the invention, an additional step includes processing the electrical signals for determination of analyte presence.

According to still another aspect of the invention, the method includes the steps of serially diluting a sample and exposing the serial dilutions to a plurality of sensor strips for the determination of analyte concentration range.

BRIEF DESCRIPTION OF THE DRAWING

For a better understanding of these and other objectives of the present invention, reference is made to the following detailed description of the invention, by way of example, which is to be read in conjunction with the following drawings, wherein.

DESCRIPTION OF THE PREFERRED EMBODIMENT

Figure 1:
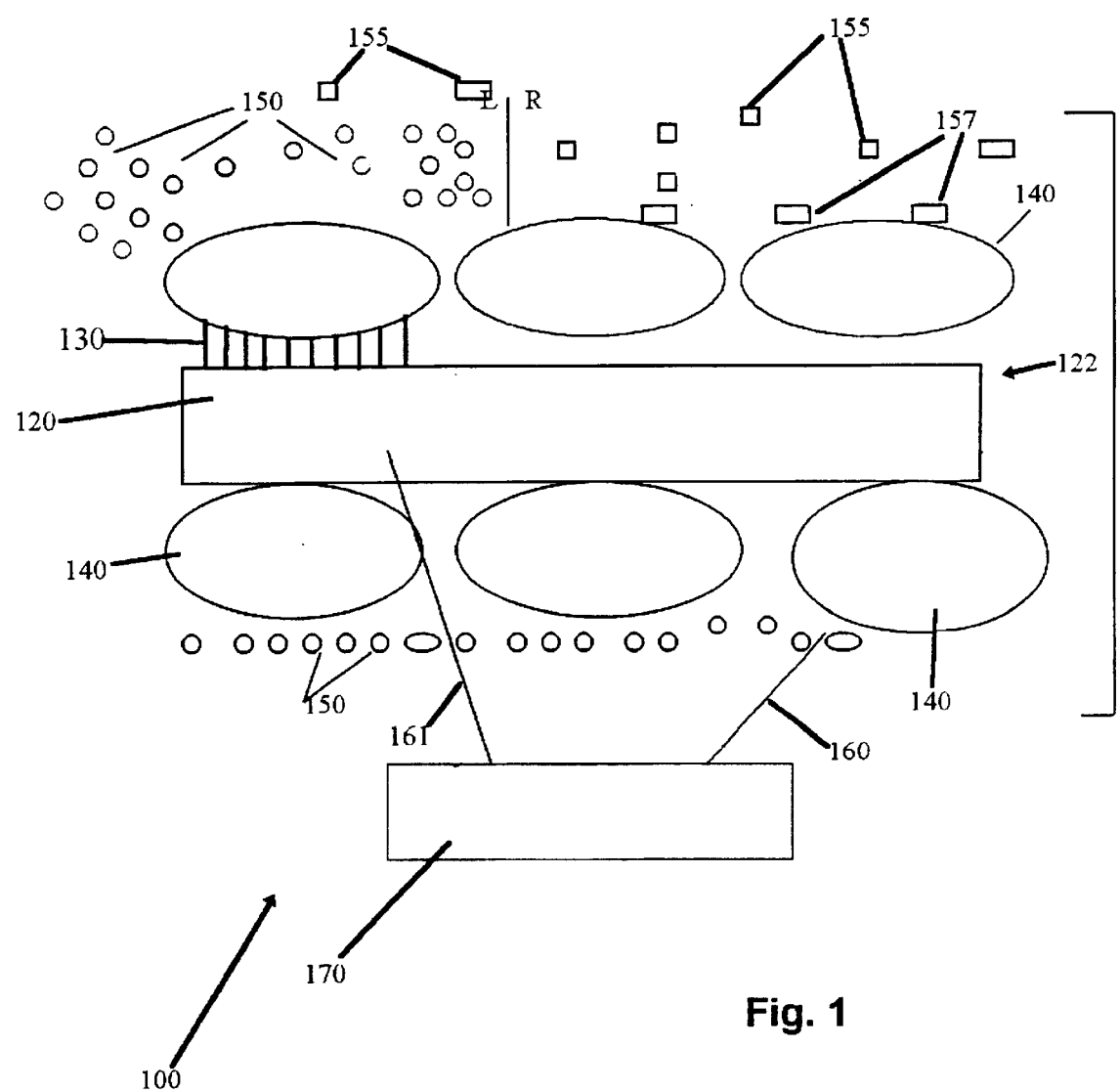
FIG. 1 is a schematic view of a sensor detection system 100 in accordance with the invention in which a sensor strip 122 comprised of base member 120, self-assembled monolayer 130, macromolecular layer 140 and packaging layer 150 forms a closed electrical circuit with electrodes 160 and 161, and detection unit 170.

Without being bound by any particular theory, the following discussion is offered to facilitate understanding of the invention. The sensor design disclosed herein is based on de novo electrical signals generated in a sensor strip as a function of analyte presence. The sensor utilizes a novel method of detecting an analyte wherein macromolecular binding agents are first immobilized proximate an electrically conductive base member. De novo electrical signals such as current, magnetic field strength, induced electromotive force, alternating voltage or changes in impedance or resistance, signal sign switching, signal frequency, electrical noise and components thereof can be monitored for change during exposure of the macromolecular binding agents to a sample that may contain target analyte. In the aforementioned PCT application, certain aspects of electrode-sensor strip contact were not fully described. In the present invention, the advantages of particular forms of sensor strip contact are disclosed more fully. Specifically, a resistive or semiconductive element may be integrated into a sensor strip, a detection unit or its associated electrodes in order to facilitate signal measurement.

Referring now to FIGS. 1–4, a typical sensor detection system 100 comprises (i) a sensor strip 122; (ii) a detection unit 170 for the detection of one or more electrical signals generated internally in the sensor strip 122; (iii) electrically-passive electrodes 160, 161 to provide contact between the sensor strip 122 and the detection unit 170. In some preferred embodiments, there can be (iv) a resistive element 299 (FIG. 2) or semiconductive element 398 (FIG. 3) in the sensor circuit comprised of the sensor strip, electrodes, and detection unit. The detection unit 170 may also serve to ground the sensor strip 122 prior to measurement, so that stray signals are removed prior to exposure of sample to the sensor strip 122. Such grounding may be performed either through an electrode or a separate contact between the detection unit 170 and the sensor strip 122 (not shown). Grounding may also be performed at times during sensor action so as to enhance signal quality and/or increase signal redundancy. In other preferred embodiments of the invention a computer 480 for processing the induced signal (FIG. 4) or a component thereof may be included. Additionally, the computer 480 may be used for controlling sample handling, serial dilution and monitoring of the unprocessed signal or the processed signal. Alternatively, an external electrical signal may be applied to the sensor strip, and the exit signal monitored for the presence and magnitude of the internally-generated electrical signal.

According to a method of the invention, one contacts equipotential passive leads of a detection unit to a sensor strip and then measures an electromotive force (emf), current, or other electrical signal internally-generated in the sensor strip as a function of analyte interaction with the sensor strip. A resistive or semiconductive element placed in the closed electrical circuit formed by the sensor strip, two passive electrodes, and detection unit aids in signal detection. Placement of the resistive or semiconductive element between at least one electrode and the sensor strip (see FIGS. 2, 3 and 6) is optimal.

As described in the noted PCT application, the methodology of detection is very sensitive. Specific detection of pathogenic bacteria in a complex meat matrix was performed within two minutes at 1–10 cells per milliliter of sample (concentration determined afterwards by plating). Measurement of internally-generated (de novo) current or voltage in a sensor strip according to the present invention allows for rapid, specific and sensitive determination of analyte presence.

In the following description, numerous specific details are set forth in order to provide a thorough understanding of the present invention. It will be apparent, however, to one skilled in the art that the present invention may be practiced without these specific details. In other instances well-known circuits and control logic have not been shown in detail in order not to unnecessarily obscure the present invention.

Certain terms are now defined in order to facilitate better understanding of the present invention. An "analyte" is a material that is the subject of detection or quantification. A "base member" or base layer is a solid or liquid element on or near which macromolecules can be physically or chemically immobilized for the purpose of sensor strip construction. Conducting and semiconducting foils, coatings, thin-films, inks, and solid pieces are particularly preferred for the role of base member.

"Macromolecules", "macromolecular binding agents", "binding agents" or "macromolecular entities" can be any natural, mutated, synthetic, or semi-synthetic molecules that are capable of interacting with a predetermined analyte or group of analytes at a level of specificity.

A self-assembled monolayer ("SAM") is herein defined as a class of chemicals that bind or interact spontaneously or otherwise with a metal, metal oxide, glass, quartz or modified polymer surface in order to form a chemisorbed monolayer. As the phrase "self-assembled" implies, a self-assembled monolayer is formed from molecules that bond with the surface upon their direct contact from solvent, vapor, or spray. As the word "monolayer" implies, a self-assembled monolayer possesses a molecular thickness, i.e., it is ideally no thicker than the length of the longest molecule used therein. In practice, this may not be the case, but a thicker chemical layer between macromolecules and base member is acceptable for sensor construction.

"chemical entity" is a layer other than a SAM that is disposed proximate the base member. It may serve to partially insulate the base member from direct contact from a detection unit and as such, the chemical entity may serve as a resistance-modifying element as defined below. A chemical entity may be deposited on or near one or both sides of a base member by any means and may also serve in the role of resistance-modifying element disposed between base member and detection unit.

A "packaging layer" is defined as a chemical layer disposed above the macromolecules. The packaging layer may aid in long term stability of the macromolecules, and in the presence of a sample that may contain analyte of interest, the packaging layer may dissolve to allow for rapid interaction of analyte and binding agents. The packaging layer may also serve in conjunction with the charged macromolecules in the role of a resistance-modifying element. Such may be the case when a sensor is coated equally on both sides with SAM's (or chemical entities), macromolecules, and packaging layers.

A "sensor strip" is defined as a minimum of a single base member and associated macromolecule or macromolecules. If multiple macromolecular entities, SAM, chemical entity, packaging layer or other layers are physically associated with the base member, then they are included in the term "sensor strip". In some preferred embodiments of the invention sensors strips are un-powered, that is, no electrical signal is applied to them. In other preferred embodiments the sensor strip may be powered through application of voltage, current, or other electrical signal to the sensor strip. A "sensor element" is defined minimally as a base unit and a macromolecule. A "base unit" is a solid or liquid element on or near which macromolecules can be immobilized for direct detection of analyte-responsive magnetic flux, as described below.

An "electrode" or "lead" is a wire, electrical lead, connection, electrical contact or the like that is attached at one end to a detection unit and contacted at the other end directly or indirectly to a sensor strip. Contact to sensor strip is generally electrically passive in nature and occurs at two positions. One of the electrodes may serve as an electron sink or electrical ground. The electrodes may be prepared from either conducting or semiconducting materials or a combination thereof. The electrodes are generally equipotential. In preferred embodiments employing electrically passive electrode contact with the sensor strip, neither electrode is used to deliver an electrical signal to the un-powered sensor strip.

The terms "internally-generated" and "de novo" electrical signals are used with respect to the electrical arts. Specifically by these terms it is intended to exclude oxidation-reduction chemistries and electrical phenomena resulting directly or otherwise from the obligate application of an external electrical or electromagnetic signal. An internally-generated or de novo electrical signal is one that is produced in the sensor strip without any required application to the sensor strip of electrical or electromagnetic signal. Additionally, there is no oxidative transfer of electrons between the base member and binding agent, analyte, or medium.

A "detection unit" is any device or material that allows for the detection of one or more electrical signals internally-generated in the sensor strip. The detection unit is generally contacted to a sensor strip at two positions through passive contact of equipotential electrodes.

The detection unit may simultaneously measure more than one type of signal and it may be contacted to a plurality of sensor strips. Additionally, it may further process the signal or a component thereof for the purpose of analyte detection and concentration range determination For example voltage sensitive dyes or materials could serve as the detection unit.

"Resistive element" and "semiconductive element" refer to resistance-modifying elements that are included in a "sensor circuit" that minimally includes one such element in addition to a base member and a detection unit. The purpose of such element is to aid in facile signal capture. The resistive element may be a resistive thin coating or other material whose presence between a base member and a detection unit facilitates measurement of de novo electrical signals in a sensor strip. A "semiconductive element" is a semiconductor that serves the role of a resistance-modifying element between the base member and the detector unit. The presence of analyte leads to augmented internally-generated electrical signals in a sensor strip. The de novo electrical signal is most easily measured if there is a resistive or semiconductive element or layer between the base member and the detection unit. Examples of appropriate resistive and conductive elements include, but are not limited to, non-conductive or dielectric coatings, organic and inorganic semiconductors, and the like. Semiconducting, doped-silicon is particularly preferred and can be placed between one or both detection unit electrodes and a sensor strip. Contact between a sensor strip and a resistive or semiconductive element may be facilitated by the presence of an adhesive agent between the two components. Resistive or semiconductive elements may be incorporated directly into detection unit, associated electrodes or sensor strips and are shown as distinct elements in the accompanying diagrams for the purpose of convenience only.

Referring again to FIG. 1, which schematically illustrates a preferred embodiment of the invention, free analyte 155 is disposed proximate a sensor strip 122 prior to (left side of figure, labeled "L") and after (right side of figure, labeled "R") dissolution of packaging layer 150. The analyte (shown as free analyte 155, and analyte 157 interacting with the macromolecular layer 140) can be a member of any of the following categories, listed herein without limitation: cells, organic compounds, antibodies, antigens, virus particles, pathogenic bacteria, metals, metal complexes, ions, spores, yeasts, molds, cellular metabolites, enzyme inhibitors, receptor ligands, nerve agents, peptides, proteins, fatty acids, steroids, hormones, narcotic agents, synthetic molecules, medications, enzymes, nucleic acid single-stranded or double-stranded polymers. The analyte 155 can be present in a solid, liquid, gas or aerosol. The analyte 155 could even be a group of different analytes, that is, a collection of distinct molecules, macromolecules, ions, organic compounds, viruses, spores, cells or the like that are the subject of detection or quantification. Some of the analyte 157 physically interacts with the sensor strip 122 after dissolution of the packaging layer 150 and causes an increase in internally/generated electrical signals measured in the sensor strip 122. Contact of electrodes 160 and 161 to sensor strip 122 allows for measurement of such a de novo electrical signal that is responsive to analyte presence. There is no requirement for application of a voltage or other electrical signal to the sensor strip 122 prior to or during measurement of internally-generated electrical signals by the detection unit 170. In some preferred embodiments, one may apply such an external signal, in which case the de novo electrical signal generated in the sensor system and responsive to analyte presence will alter the exit signal in such a system.

Examples of macromolecular entities suitable for use in the sensor detection system 100 include but are not limited to enzymes that recognize substrates and inhibitors; antibodies that bind antigens, antigens that recognize target antibodies, receptors that bind ligands, ligands that bind receptors, nucleic acid single-strand polymers that can bind to form DNA-DNA, RNA-RNA, or DNA-RNA double strands, and synthetic molecules that interact with targeted analytes. The present invention can thus make use of enzymes, peptides, proteins, antibodies, antigens, catalytic antibodies, fatty acids, receptors, receptor ligands, nucleic acid strands, as well as synthetic macromolecules in the role of the macromolecular layer 140. Natural, synthetic, semi-synthetic, over-expressed and genetically-altered macromolecules may be employed as binding agents. The macromolecular layer 140 may form monolayers as in FIG. 1, multilayers or mixed layers of several distinct binding agents (not shown). A monolayer of mixed binding agents may also be employed (not shown).

The macromolecule component is neither limited in type nor number. Enzymes, peptides, receptors, receptor ligands, antibodies, catalytic antibodies, antigens, cells, fatty acids, synthetic molecules, and nucleic acids are possible macromolecular binding agents in the present invention. The sensor method may be applied to detection of many classes of analyte because it relies on the following properties shared by substantially all sensor detection systems:

(1) that the macromolecules chosen as binding agents are highly specific entities designed to bind only with a selected analyte or group of analytes;

(2) that a sensor strip including a macromolecular binding agent and an electrically-conductive base member can exhibit internally-generated electrical signals;

(3) that the internally-generated electrical signals are responsive in magnitude, sign, and or frequency to the presence of analyte in a sample exposed to sensor strip; and (4) that the internally-generated electrical signals can be detected in a closed electrical circuit comprised of sensor strip, a detection unit, associated electrodes, and a resistive or semiconductive element.

Figure 2:
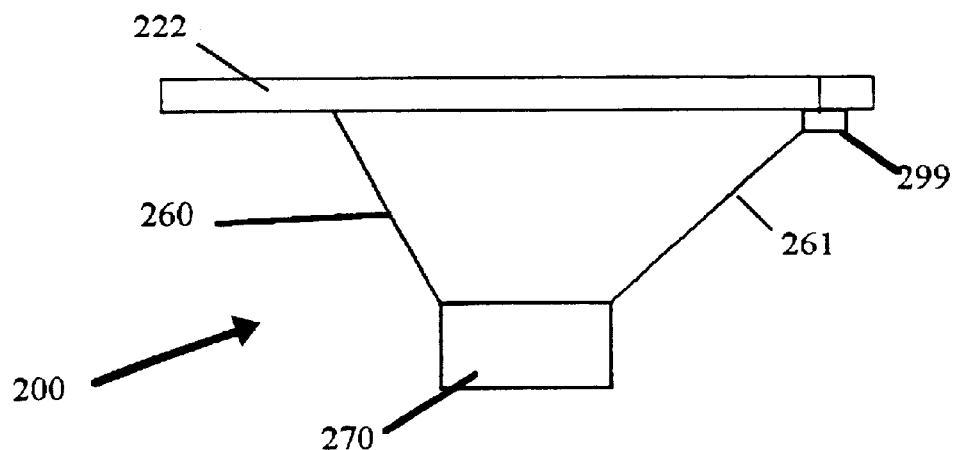
FIG. 2 is a schematic view of a first alternate embodiment of a sensor system detection 200 in accordance with the invention in which a resistive element 299 is placed in the closed sensor circuit of sensor strip 222, electrodes 260 and 261 and detection unit 270.

For example, in the alternate embodiment of FIG. 2, which is generally similar to the first embodiment, an induced current may be measured in a closed electrical circuit that contains a sensor strip 222, electrodes 260 and 261, detection unit 270, and a resistive element 298. A relatively small background induced current is present in the circuit due to the macromolecules present on the sensor strip. The background current may optionally be zeroed by grounding of the sensor strip prior to sample exposure. Presence of analyte in sample causes increased induced current as measured by detection device 270 that is passively contacted through electrodes 260 and 261 to the sensor strip 222. The resistive element need not contribute significant resistance to the overall detection circuit, but its presence between sensor strip and detection electrodes is of importance for successful signal capture. It is possible to optionally apply a current to the sensor system shown in FIG. 2, in which case the exit current would be the sum or difference between the applied current and the analyte-responsive internally-generated current.

Referring again to FIG. 1, the macromolecular layer 140 and the packaging layer 150 may serve the role of a resistance-modifying element. Since the packaging layer 150 and the macromolecular layer 140 are uneven in their surface properties, excessive electrode pressure during fabrication or from an ad hoc application of the electrodes 160, 161 during a sensing operation can short out the circuit. This short occurs as a consequence of both electrodes 160, 161 being in a nonresistive mode of contact with the base member 120, which under certain non-grounded, conditions, can lead to a condition of no signal. Thus, a resistance-modifying element, such as semiconductive element 398 (FIG. 3) or a resistive element 299 (FIG. 2) is included in the sensor circuit to obviate this problem and additionally to remove the need for deposition of an additional conductive layer on the sensor strip. In many applications, the sensor is disposable, and is intended be provided without the detection unit 170, in which case the detection unit 170 is external to the sensor, and the resistance-modifying element is accessible to the detection unit 170 using electrical contact points, pin-outs, or the like.

The ohmic resistance of the resistance-modifying element does not have to be very high and is preferably between about 1 and 20 ohms. Values of 1–12 ohms have been found to work well in prototypes. For example in the embodiment shown in FIG. 6, the adhesive agent 633 has been realized as Scotch brand glue stick (product number 6008), which has been applied to sensor strips and has served the role of both adhesive agent and resistive element. Alternatively, one or more resistors may be placed between base element and detection unit in order to effect resistance modification.

The broad and generally applicable nature of the present invention is preserved during binding of the macromolecular layer 140 (FIG. 1) in proximity to the base member 120 because binding can be effected by either specific covalent attachment or general physical absorption. It is to be emphasized that the change in de novo signal that is associated with analyte presence does not depend on any specific enyme chemistries, optical effects, fluorescence, chemiluminescence, oxidation/reduction phenomena or applied electrical signals. Additionally, there are no reference electrodes, and the two detection unit electrodes are generally equipotential prior to measurement of signal internally-generated in the sensor strip. These features are important advantages of the present invention. Additionally, during operation of the sensor according to the invention, current is actually generated, and the generated electricity may be of use in powering devices such as certain components of the sensor system itself.

With respect to electricity generation, the generator design disclosed herein is based on electromagnetic induction of electrons in conducting materials when said electrons are exposed to fluctuating macromolecular electrostatic fields. The generator utilizes a novel method of generating electricity wherein macromolecular binding agents are first immobilized proximate an electrically conductive base element. The bound macromolecules are always moving; the motion of the electrostatic fields associated with the macromolecules serves to generate an induced electrical signal in the base element. The fluctuating electrostatic fields generate fluctuating magnetic fields, and these fluctuating magnetic fields induce electron motion in the base member. When the base member is part of an electric circuit, induced current will flow. The process of electromagnetic induction by mechanical means was first described by Faraday in 1831, and in the present invention, biological and synthetic macromolecules serve to generate the fluctuating magnetic fields required to induce current flow in a conductive base element.

Figure 10:
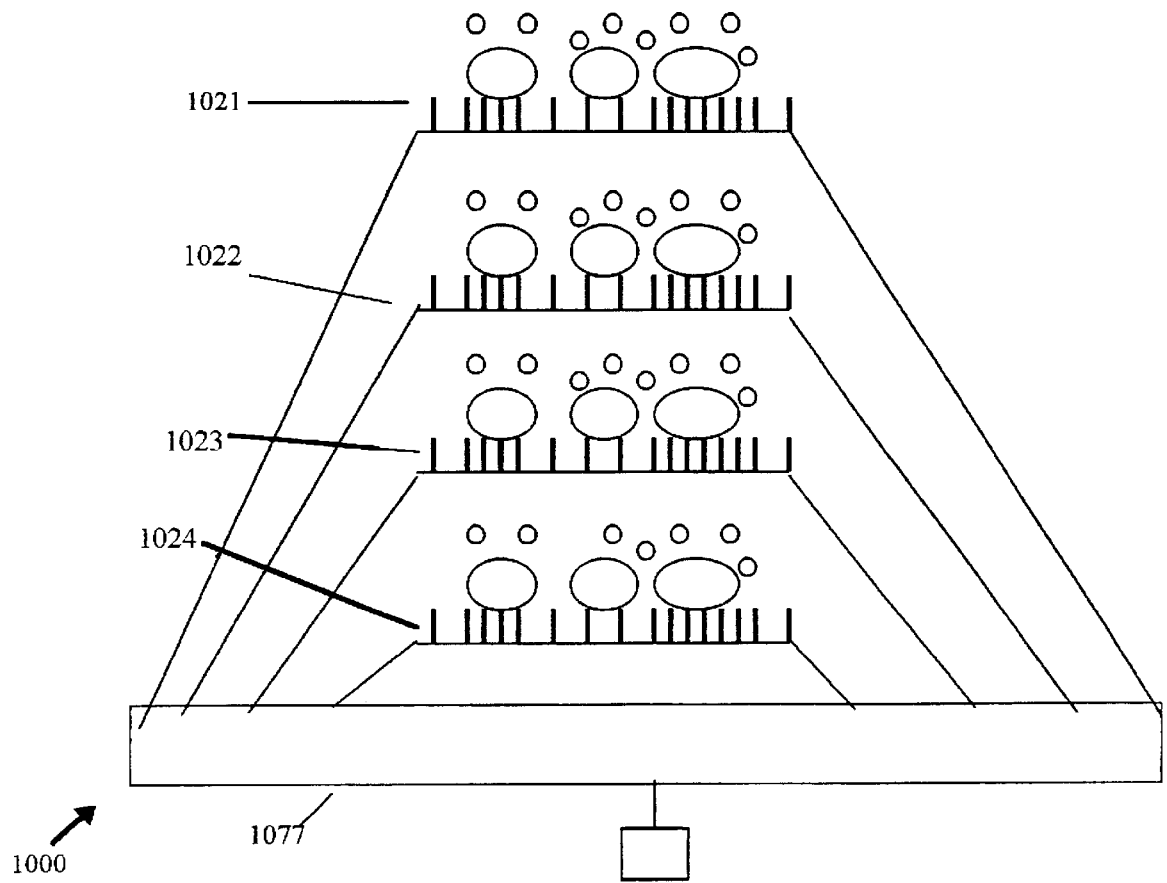
FIG. 10 is a schematic view of an electrical generator based on de novo electrical signals resulting from interaction of macromolecules with cognate molecules.

A typical generator strip comprises (i) a multilayer substrate comprising a conducting base element or layer and an optional chemical layer;(ii) at least one macromolecule that displays a level of affinity of interaction toward a predetermined cognate molecule or group of cognate molecules; and (iii) electrical leads contacted to the base element generally at two positions. In FIG. 10, four such generator strips 1021–1024 are shown attached through independent sets of leads to a rectifier-type device 1077 for the production and utilization of electrical energy.

The generator exploits the phenomenon of electromagnetic induction, the process by which fluctuating magnetic fields can induce electron motion in nearby electrically conducting materials. Since the device works on physical properties shared by nearly all macromolecules, the methodology is appropriate for a large variety of macromolecule classes. Additionally, charged or polar synthetic binding agents are appropriate for use in electricity generation. The one requirement for a macromolecular moiety is that it demonstrates a level of specificity of interaction with a predetermined cognate molecule or group of cognate molecules. The physical motion of macromolecules (proteins and DNA) immobilized in proximity to solid supports is of importance to the present generator methodology and has been described in the scientific literature (Proteins on insulating mica: Thomson, N H, et al., *Biophysics Journal* 70:2421–2431 (1996); DNA on insulating mica: Bezanila, M, et al. *Biophysics Journal* 67: 2454–2459 (1994)).

According to preferred embodiments of the generator, in order to generate electricity, one first immobilizes one or more biological or synthetic macromolecules in proximity to an appropriately conductive base element. A change in motional behavior of the binding agent or addition of electrostatic material associated with the cognate molecule causes an increased electromagnetic induction in the base element and thus allows for triggered increases in current production by the device. Experience of the inventor has shown that non-specific interactions of macromolecules and sample do not produce a significant induced current. Such conclusions are based on studies in complex matrices such as blood plasma, milk, stool, and ground beef homogenized in phosphate buffer. This point is significant as the generator may be employed in waste streams or industrial run-offs, converting waste products into electricity.

The present invention provides for the generation of electrical energy by the mechanical motions of charged/polar macromolecules. The amount of energy can be fixed by the specific macromolecule/molecule system selected as well as the number of base elements employed in a multiplexed device. The number of macromolecules bound in proximity to a conducting base element is dependent on the size of the specific macromolecules as well as packing efficiencies. For a macromolecule such as an enzyme that is 100 Angstroms on a side, and at high packing efficiencies, $10^{12}$ macromolecules can be immobilized per square centimeter of base element. Paul Hansma and his colleagues (Radmacher, et al. cited previously and public seminar, Jerusalem, Israel 1996) have shown by atomic force microscopy (AFM) that the enzyme lysozyme experienced approximately 1.5 nanometer vertical and 10 nanometer horizontal displacements during its catalytic cycle. The enzyme performed its reaction at a rate of 20 turnovers per second. Thus, one could expect the theoretical net motion of $10^{12}$ macromolecules bound in proximity to a square centimeter of base element to be 100 kilometers per second. This value assumes a net motion of 5 nanometers per cycle, 20 cycles per second, and that all of the macromolecules are engaged in catalysis. In reality, the density of macromolecules may be lower, the amount of motion per cycle could be less, less than 100% of all enzyme molecules may be functioning, and enzyme motions are not coordinated so a real "net" distance would be less. Still, the exercise is instructive in demonstrating the tremendous amount of mechanical motion of charged bodies, and the potential for converting those motions into electrical energy. The motion of macromolecule-associated electrostatic fields creates fluctuating magnetic fields that induce current flow in the base element. Enzymes, due to their substrate-responsive motional behavior, are preferred macromolecules for use in the macromolecular layer according to the present invention. Enzyme turnover rates as high as of 10,000 conversions per second have been documented.

Referring again to FIG. 1, the macromolecular layer 140 used in the present sensor invention is located proximate base member 120. A chemical entity or SAM 130 (shown at the left side of FIG. 1) may optionally be disposed between the base member 120 and the macromolecular layer 140, or the macromolecular layer 140 could be positioned on an element (not shown) that is separate from the base member 120 itself. For the purposes of this invention, "proximate"

with respect to macromolecule disposition relative the base member is defined as any distance that allows for analyte-responsive generation of a de novo electrical signal in a sensor strip comprised of the macromolecules of the macromolecular layer 140 and the base member 120.

The detection unit 170 is any device or material that can detect one or more de novo electrical signals in a sensor strip 122 as a result of the latter's exposure to a sample that contains analyte 155. Examples of such signals include but are not limited to current; magnetic field strength; induced electromotive force; voltage; impedance; signal sign; frequency component or noise signature of a predetermined electrical signal propagated into a sensor strip at a first location and received at a second location. While the detection unit 170 may be a digital electrical metering device, it may also have additional functions that include, but are not limited to sensor strip grounding, data storage, data transfer, data processing, alert signaling, command/control functions, and process control. Detection units may be contacted through "leads", realized as electrodes 160 and 161 to one or a plurality of sensor strips 122. Contacts between the sensor strip 122 and detection unit 170 are generally at two positions 165, 167 on the sensor strip.

Figure 5:
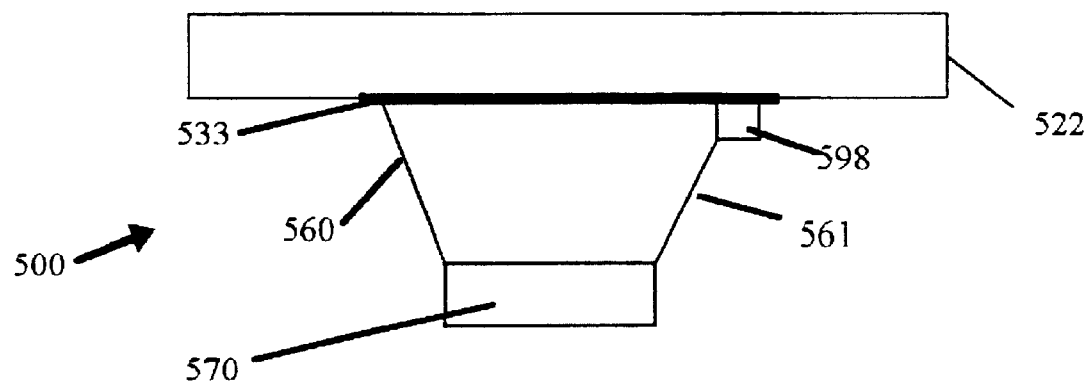
FIG. 5 is a schematic view of a fourth alternate embodiment of a sensor detection system 500 in accordance with the invention in which an adhesive agent 533 is present on a sensor strip 522 and aids in contact with detection unit 570 electrode 560 and resistance modified electrode 561.

Referring to FIG. 5, if the detection unit 570 is a voltmeter device with very high internal impedance, one can measure an internally-generated emf directly through passive contact of electrodes 560 and 561 to the sensor strip. A semiconductive element 598 incorporated into electrode 561 allows for measurement of the induced emf in sensor strip 522. Adhesive agent 533 aids in good contact between the sensor strip 522 and detection unit 570 electrodes 560 and 561.

Figure 3:
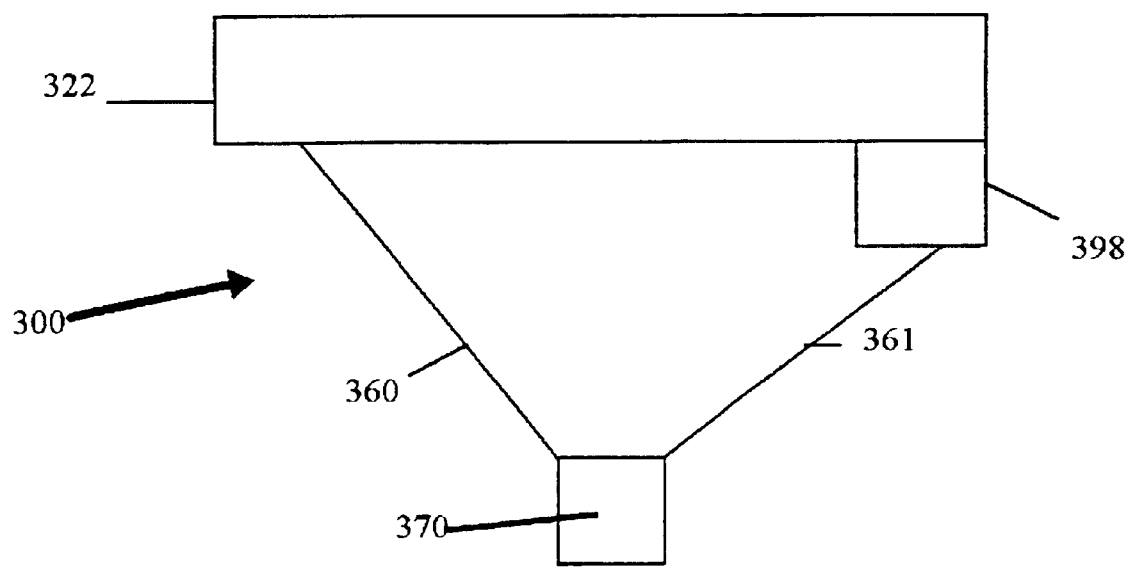
FIG. 3 is a schematic view of a second alternate embodiment of a sensor detection system 300 in accordance with the invention in which a semiconductive element 398 is included in the closed sensor circuit of sensor strip 322, electrodes 360 and 361 and detection unit 370.

The internally-generated electrical signal is measured in a sensor circuit that includes at least one resistive element 299 (FIGS. 2, 6) or a semiconductive element 398 (FIG. 3). Baseline readings may be determined from a sample that lacks target analyte or analytes or for a grounded sensor strip prior to sample exposure. For example, milk that lacked any antibiotics, registered internally-generated (de novo) voltage readings of 8 millivolts in a sensor strip composed of aluminum foil, carboxylic acid-based SAM's, penicillnase (an enzyme that recognizes the analyte, penicillin), and the packaging layer of sodium chloride and glucose. Milk spiked with penicillin at 4.3 parts-per-billion (weight-to-volume) yielded an internally-generated signal of 371 millivolts.

Figure 4:
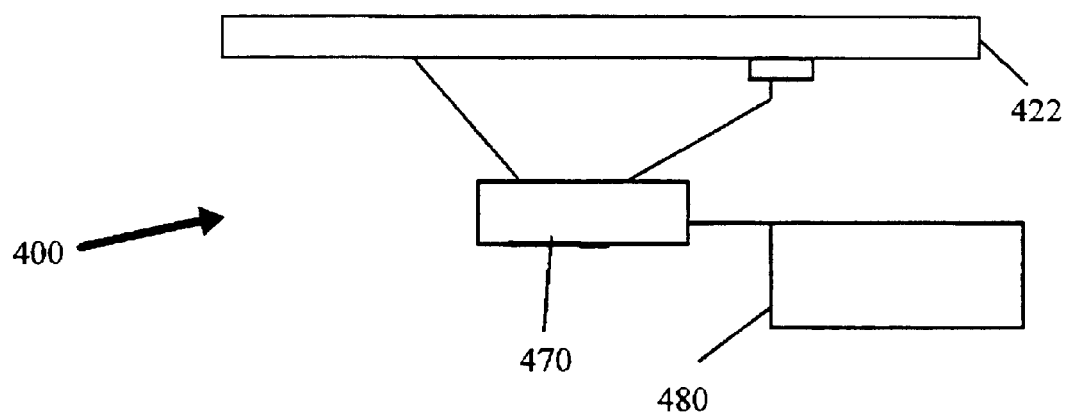
FIG. 4 is a schematic view of a third alternate embodiment of a sensor detection system 400 in accordance with the invention in which a computer 480 for data processing is attached to detection unit 470.

The specific design of a detection unit depends on what quantity or quantities (current, magnetic field flux, frequency, impedance, etc.) are being observed. The detection unit may be integrated into a computer 480 as shown in FIG. 4 or other solid-state electronic device for easier signal processing and data storage. The same or a different computer may be used to control sample application or sample serial dilution in order to monitor both sample manipulation as well as the internally-generated electrical responses in a single or multiplexed sensor strip arrangement. The detection unit may also be a voltage-sensitive dye or colored material.

With respect to quantification of analyte presence, one may employ serial dilution of sample with analyte detection as described in the present application. Specifically, a sample of interest is serially diluted in a serial dilution unit 1190 (FIG. 11), and each dilution is exposed either to one sensor strip of base member plus macromolecules or to independent sensor strips 1121–1124. As all of the strips are generally of identical embodiment, they exhibit identical sensitivity. One determines the limit of sensitivity for sensor strips prior to an experiment.

Thus, when one exposes the serial dilutions to sensor strips, there will be a response in those samples that have analyte present at or above the lower limit of sensitivity. One may thus calculate the concentration of analyte as a function of the known sensitivity of the system and the highest level of dilution that still yields a signal. One may alternatively use various embodiments for the sensor strips (not shown). In such a case, the sensitivity of each sensor strip must be determined prior to use.

As described in the patent application PCT/IL99/00309, the methodology of detection is very sensitive. Knowledge of absolute sensitivity of a given embodiment is critical for serial dilution-based quantification, as one may calculate an analyte concentration as a function of serial dilution. Serial dilution can be controlled by a serial dilution unit, (SDU), 1190 (FIG. 11) and pre-determined sensor strip sensitivity. Thus, if one dilutes a sample one thousand fold, and the known sensitivity of a sensor strip is 1 cell per milliliter, then a positive score would imply that at least 1000 cells per milliliter were present in the original sample. If a further ten-fold dilution yields no score, then one knows that the concentration of cells in the initial sample 15 was between one thousand and ten thousand cells per milliliter. A finer serial dilution may yield a more precise value.

Referring again to FIG. 1, an optional packaging layer 150 for the sensor detection system 100 is a layer of water-soluble chemicals deposited above the immobilized macromolecules of the macromolecular layer 140. The packaging layer 150 is deposited by soaking or spraying methods. The packaging layer 150 serves to stabilize the macromolecular layer 140 during prolonged storage. In the absence of a packaging layer, oil and dirt may build up on the macromolecular layer 140 and may interfere with the rapid action of the sensor system. Glucose and a salt, such as sodium chloride, are typically used for the packaging layer 150 so as to guarantee their dissolution in aqueous samples, and thus facilitate direct interaction between macromolecular binding agent (macromolecular layer 140) and analytes 157. Additionally, for sensor strips that are coated equally on both sides, the packaging layer may also serve as part of a resistive element 299 (FIG. 2), as electrons may pass through non-conducting material contained in the packaging layer. Electrode 161 contacts this layer at position 167. Other hydrophilic chemicals may be chosen for this role. When the packaging layer 150 dissolves, the binding agents are free to immediately interact with analyte 155 and 157, as shown on the right side of FIG. 1. Water-soluble polymers, sugars, salts, organic, and inorganic compounds are all appropriate for use in preparation of the packaging layer 150. Specific features of the detection unit such as arrangements of electrodes and modes of response to analyte presence may be found in the PCT patent application noted previously. Leads may be contacted to end or internal regions of a sensor strip. Contact of at least one lead to an end of a strip appears to aid in signal acquisition. The detection unit may also include a mixing element or chamber in order to aid in bringing analyte to macromolecules.

There are several points to note in regards to the method of detection of analyte as performed by the present invention. Conducting materials are normally at a single electrical potential (voltage) at all points along their surfaces. In the present invention, interactions of macromolecular binding agents with target analytes allow for internal generation of electrical signals in a sensor strip composed minimally of a conductive base member and an associated macromolecular binding agent. A sensor circuit that includes sensor strip, a detection unit, detection unit electrodes and a resistance-modifying element allows for facile detection of the electrical signals generated in the sensor strip. Readings as high as 500 millivolts or 10 microamperes have been routinely recorded in functioning analyte detection systems according to the invention, employing enzyme, nucleic acid, receptor, antibody, and synthetic binding agents.

The implications of the analyte detection methodology are significant. Firstly, detection can take place far away from the point of macromolecule-analyte contact, as the internally-generated electrical signals are propagated throughout the conductive portions of a sensor strip. This fact allows for closed-package "food sensing" or the sensing of potentially hazardous samples, e.g. blood in closed containers. One portion of the sensor contacts the material of interest, while detection of analyte-responsive de novo electrical signals occurs between two points on the exposed portion of the sensor strip. This remote detection capability is an important feature of the present sensor. The implications are that nearly any material that can be recognized at a level of specificity by a peptide, protein, antibody, enzyme, nucleic acid single strand, synthetic binding agent, or the like can be detected and quantified safely in food, body fluids, air or other samples quickly, cheaply, and with high sensitivity. Response is very rapid, generally less than 90 seconds. Cost of manufacture is low, and sensitivity has been shown to be very high.

Figure 12:
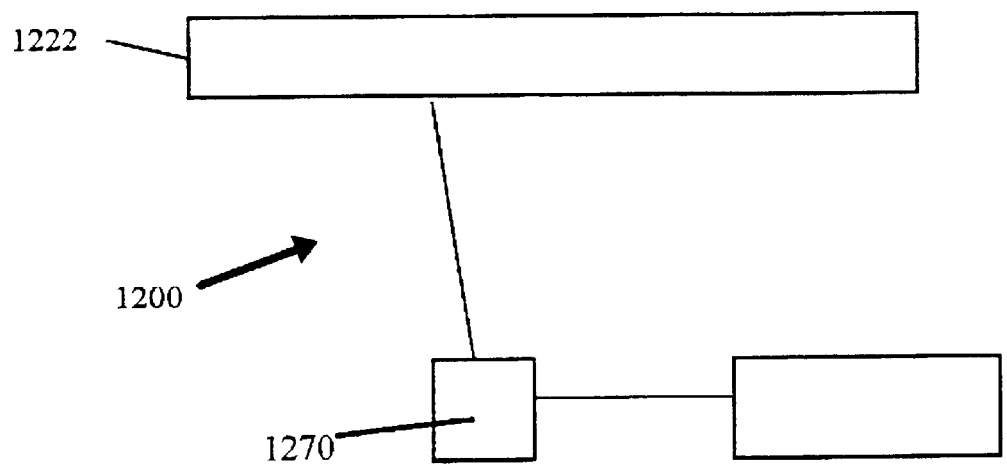
FIG. 12 is a schematic view of a sensor system for the detection of analyte through the non-contact monitoring of magnetic field flux resulting from the interaction of macromolecule with target analyte.

It is believed that the internally-generated electrical signals result specifically from changes in magnetic fields associated with the binding elements. According to a method of magnetic flux detection, one may provide a non-conducting "base unit", possibly an inexpensive organic polymer. Macromolecules are immobilized in proximity to the base unit. As shown in FIG. 12, a sample that may contain a target analyte is contacted to the sensor element 1222 of base unit and macromolecules and a detection unit 1270 in a non-contact mode of operation detects magnetic fields or magnetic field flux that is responsive to analyte presence.

Whereas the invention described in the noted PCT application PCT/IL99/00309 made use of specifically conductive base members and detection of de novo electrical signals, the sensor element does not necessitate use of a conducting base element, and direct detection of magnetic fields may alternatively be performed in the absence of contact between a detection unit and a sensor element minimally composed of macromolecules and a base unit. A base unit may not be necessary if the macromolecules are present in a solution that contains the analyte of interest.

Magnetic field flux generated during the interaction of macromolecules and analyte may be detected without recourse to a base unit.

The present invention has several advantages compared to the known prior art:

While the sensor method disclosed in the noted co-pending PCT application that is based on detection of de novo electrical signals has allowed for rapid determination of analyte presence in complex sample matrices, the issues of electrode contact to sensor strip and sensor circuit components have heretofore not been fully described. While some embodiments, particularly involving alterations in SAM or base member have allowed for analyte detection, a goal of the present invention is to optimize the specific relationship of sensor strip to the other components of the sensor circuit. Thus, the present invention allows for analyte detection by virtue of monitoring of electrical signals internally-generated in a sensor strip and measured in a sensor circuit that includes a resistive or semiconductive element as described. Multiple base members may be employed in a single sensor strip so as to increase system detection redundancy and/or multiple analyte detection capabilities. Each sensor strip is monitored on its own sensor circuit.

In an alternate preferred embodiment, an adhesive agent 633 (FIG. 6) may be applied to a sensor strip 622 in order to facilitate strong electrical contact between it and the detection unit 670 the electrodes 660 and 661 that have been modified to include resistive elements 697, 699. The adhesive agent may also serve in the role of resistance-modifying element.

Table 1 lists some of the possible components, detectable de novo electrical or magnetic signals and target application markets relevant to the present invention. Each grouping is independent of the others and one may combine a base member, a macromolecule, and a signal for an application area of choice. The table is in no way meant to be limiting in scope or spirit of the present invention.

TABLE 1

| Base Member | Macromolecule | Signal | Application |
| --- | --- | --- | --- |
| Metal | Enzyme | Magnetic Flux | Food Safety |
| Conductive Film* | Antibody | Induced Current | Chemicals |
| Organic Conductor | Nucleic Acids | Impedance | Biologicals |
| Conductive Liquid | Fatty Acid | Resistance | Environment |
| Conductive Ink | Receptor | Sign Switching | Hygiene |
| Graphite Semiconductor | Synthetic-Molecule | Frequency | Internet |
| | Protein | Noise Signature | Genetic Testing |
| | Peptide | Electromagnetic-Induction | Diagnostics |
| | Cell | Capacitance | Process Control |
| | Catalytic-Antibody | Fourier Transform | Drug Screening |
| | Synthetic Receptor | Band-Pass Filtered | Drug Release |
| | Receptor Ligand | Magnetic Fields | Glucose Testing |
| | Antigen | Voltage | Forensics |
| | | | Veterinary-Testing |

*A conductive film can be deposited on a solid support by any means, including electroless deposition, spin coating, sputtering, vapor deposition, plating, "printing" or dipcoating.

EXAMPLE 1

Figure 7:
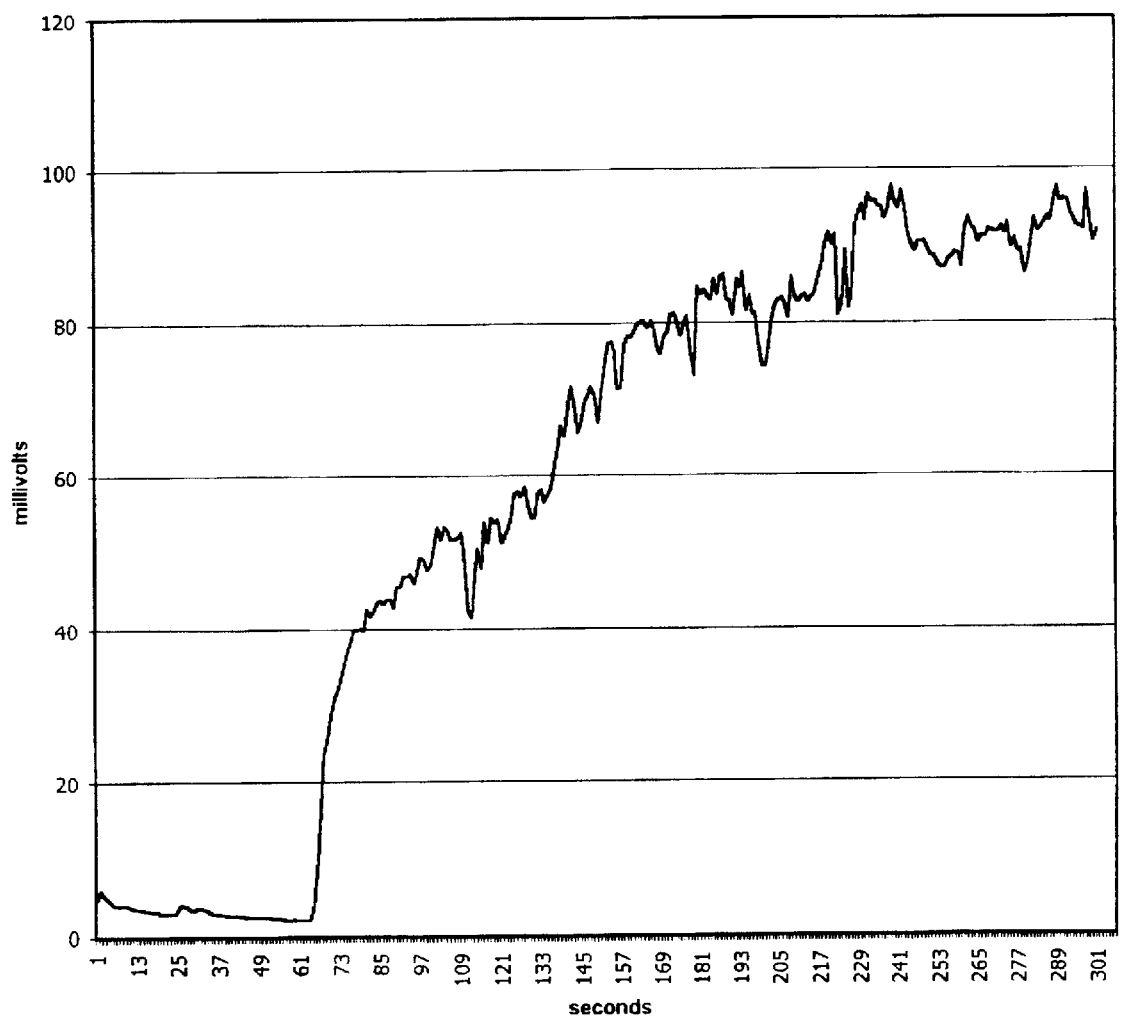
FIG. 7 is a graph of results from a sensing experiment performed with an antibiotic sensor based on the present invention.

Aluminum foil sheets were soaked overnight in an aqueous solution of parahydroxybenzoic acid and then rinsed in water. The foil sheets were then soaked in a dilute solution of penicillinase (approximately 40 minutes) and transferred to a solution of sodium cloride and sucrose (packaging layer) prior to drying under ambient room conditions. Sensor strips were cut from the sheets and used in the detection of ampicillin. The detector used was a Radio Shack multimeter (Catalogue Number 22-168A) that comes fitted with a computer cable and PC-appropriate software. The supplied leads were replaced with two banana leads that were modified for detection unit specifications. To one lead was soldered a thin metal rod (approximately 5 centimeters in length; gold-coated at the end) and to the other was soldered a gold-coated silicon wafer. The vapor-deposited gold was used to facilitate soldering of the silicon piece (approximately 1×1 cm$^2$) to the lead. The exposed side of the silicon chip was coated with UHU stick glue, and a sensor strip was pressed onto the glue-coated silicon chip. The metal rod was placed flush on top of the strip. In this example, based on the alternate embodiment shown in FIG. 3, there are two banana leads, a semiconductive silicon element, the sensor strip, and the multimeter-based detection unit. No power was applied to the sensor strip. De novo voltages were measured for a strip in air and in the presence of saline (data not shown). As the readings did not exceed 0.4 mV, the system was considered to be free of contamination and ready for analyte detection. The same saline solution was employed for dissolution of ampicillin; the ampicillin solution was used in testing the penicillinase (macromolecular binding agent)-based sensor strips. As shown in FIG. 7, a strip was tested first in air and then in the presence of the saline-ampicillin solution. The x-axis shows seconds for the experiment, while the y-axis is in millivolts. The ampicillin solution was added at approximately sixty seconds into the experiment. Significant de novo signal was recorded only and specifically when ampicillin was present in the sample.

EXAMPLE 2

Aluminum foil (Reynolds) sheet is soaked in an ethanolic solution of stearic acid. The SAM-coated foil is washed in water and then soaked in an aqueous solution of lysozyme. The sensor sheet is soaked briefly in sodium chloride and glucose and then allowed to dry. The sheet is cut into strips and the strips are packaged. For use, each strip is placed into a 1.5 milliliter Eppendorf tube. Sample that may contain bacteria, the lysozyme substrate, is added to the Eppendorf tube and the tube is closed. Two leads of a detection unit are contacted to the exposed portion of the sensor strip, and through one of the leads, one lead having a silicon semiconductor placed at its end such that the silicon chip is in direct contact with the sensor strip. When the detection unit reads a low voltage background for the strip, the sample is contacted to the strip on the inside of the Eppendorf tube, while voltage measurements are made between the two contact points between the sensor strip and the detection unit electrodes. Signals significantly above pre-determined background values imply the presence of bacteria in sample. The sensor strip may be grounded during the course of a sensing experiment; return of signal after grounding suggests that the signal is due to the action of the lysozyme macromolecules associated with the aluminum foil base member.

EXAMPLE 3

Figure 8:
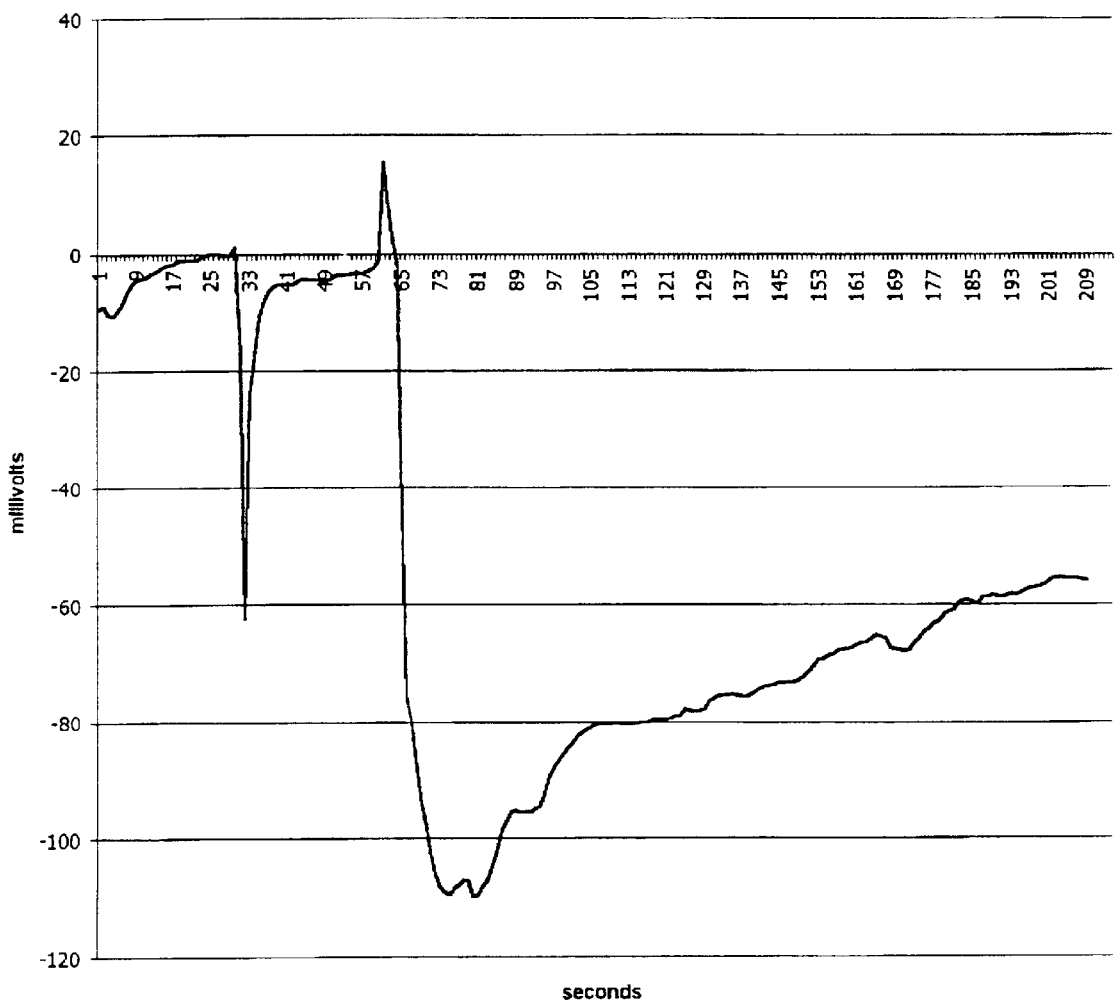
FIG. 8 is a graph of results from a sensing experiment performed with a lactose sensor based on the present invention.
Figure 9:
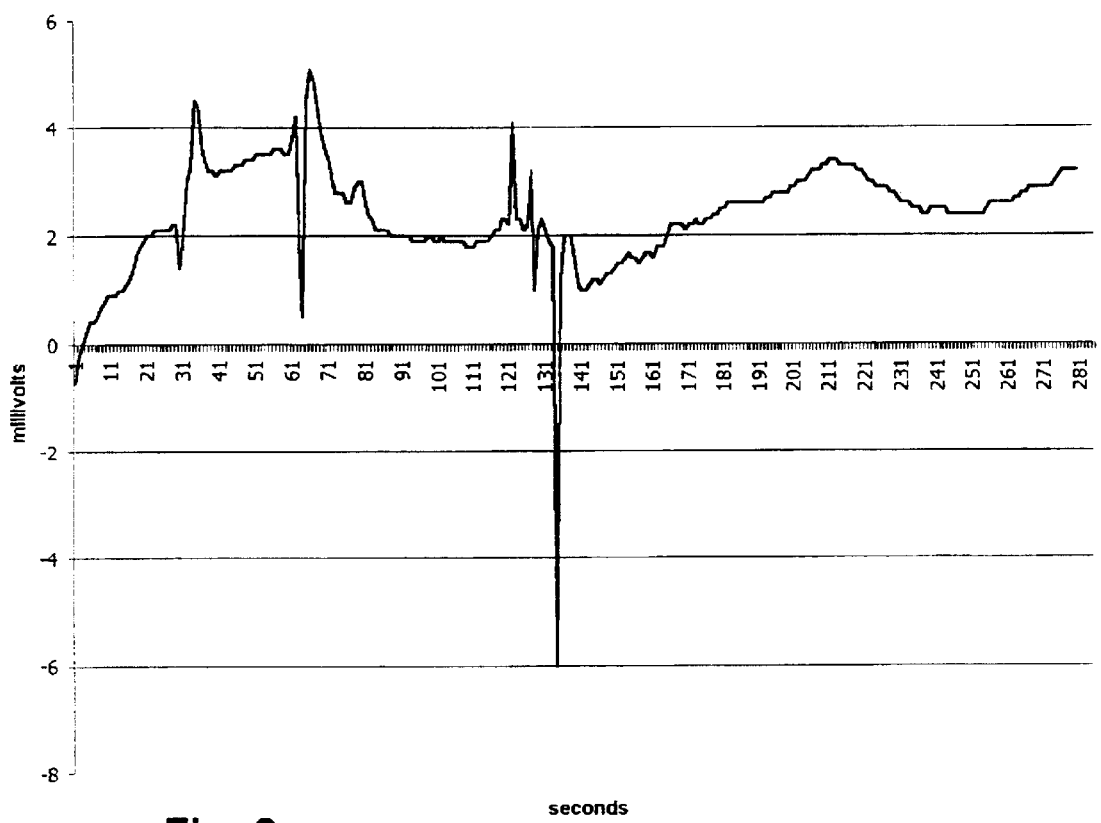
FIG. 9 is a graph of results from a sensing experiment performed with a control sensor in the presence of lactose.

Semiconductor-grade silicon was cut into chips. The chips were coated with strips of conducting silver paint. Specifically, a coat of Jeltargent conducting silver paint was applied either in a straight line or in an "L" shape. The paint was allowed to air-dry. Approximately half of the coated chips were soaked in an aqueous solution of the enzyme, lactase (beta-galactosidase) for fifty-minutes while half were left as control chips. Those that were soaked in enzyme solution were further soaked for ten minutes in a sodium chloride solution and then allowed to air dry. Thus, the sensor strip included a semiconductive layer (silicon), a base member (silver paint), macromolecular entities (lactase), and a packaging layer (sodium chloride). The detection unit, electrodes, and semiconductive element were the same as described in Example 2. Additionally, UHU glue was applied to the silicon chips (opposite the side with silver) and aided in contact of sensor strip to the semiconductive element, as shown in FIG. 5. Chips, both with and without enzyme, were exposed to saline and then to a solution known to contain lactose, the enzyme substrate. FIG. 8 shows results for a lactase-coated chip, while FIG. 9 shows the data for a control chip that lacked enzyme. In both cases, the chips were exposed initially to air, then to saline until a steady baseline had been established, and finally to a solution that contained lactose. In the experiment detailed in FIG. 8, saline was placed on the chip after approximately thirty seconds, and lactose-containing solution was then added approximately thirty seconds later (approximately one minute into the experiment). In the control experiment (FIG. 9), saline was placed on the chip after approximately one minute, while lactose-containing solution was added one minute later (two minutes into the experiment). Such experiments were performed three separate times on different chips for lactase-containing and control chips (six experiments total). The data displayed in FIGS. 8 and 9 show that the maximum readout of the control experiment lacking macromolecular binding agent was around 6 millivolts (FIG. 9), while the sensor strip that contained the enzyme lactase showed readings in excess of negative 100 millivolts (FIG. 8). Similar results were seen for the other four experiments (data not shown). No external electrical signal was applied to the un-powered sensor strip and lactase does not perform oxidation-reduction chemistry.

EXAMPLE 4

Semiconductor-grade silicon (1 cm×1 cm) is photolithographically modified to yield a structure of $5\times10^4$ aluminum wires (0.1 micron width) with 0.1 micron spacing between them. The wires are coated with a SAM prepared from an ethanolic solution of parahydroxybenzoic acid. The enzyme triosephosphate isomerase (TIM) is physically absorbed to the SAM layer, and a packaging layer of sodium chloride/glucose is deposited by soaking. The final generator "chip" has $5\times10^4$ sensor strip "lanes" of enzyme-coated conducting wires. The wires are coated at their ends with a dielectric resistance-modifying element and then contacted by electrodes that lead to a rectifier and ultimately to a load. The chip is exposed to an aqueous solution of 1 millimolar glyceraldehyde 3-phosphate (GAP), a TIM substrate. TIM interconverts GAP and product dihydroxyacetone phosphate (DHAP). The chip is sealed in plastic so that a few microliters of solution remain above the enzyme macromolecules. Current generated by the interaction of TIM with molecules of GAP and DHAP is directed by electrodes to a rectifier 1077 (FIG. 10). DC current is used to power a smart card (not shown) on which the chip is physically fastened.

EXAMPLE 5

Long graphite rods are soaked in an aqueous solution of protease enzymes. Proteases digest proteins by breaking amide linkages between amino acids. Several hundred thousand of the graphite rods are connected in parallel to a rectifier, and the graphite rods are exposed to agricultural waste streams that are rich in protein debris. Protease action on the protein (the substrate of the proteases) leads to increased motion of the charged protease molecules and thus heightened electromagnetic induction in the graphite. Current induced in the graphite is directed to a rectifier and then on to a device that processes the wastes. New proteins are always delivered to the macromolecules and the system continues to produce electricity until either the enzymes are no longer functional or fouling prevents delivery of proteins to the protease enzymes. At that time, the rods are replaced for fresh generator rods.

EXAMPLE 6

Figure 11:
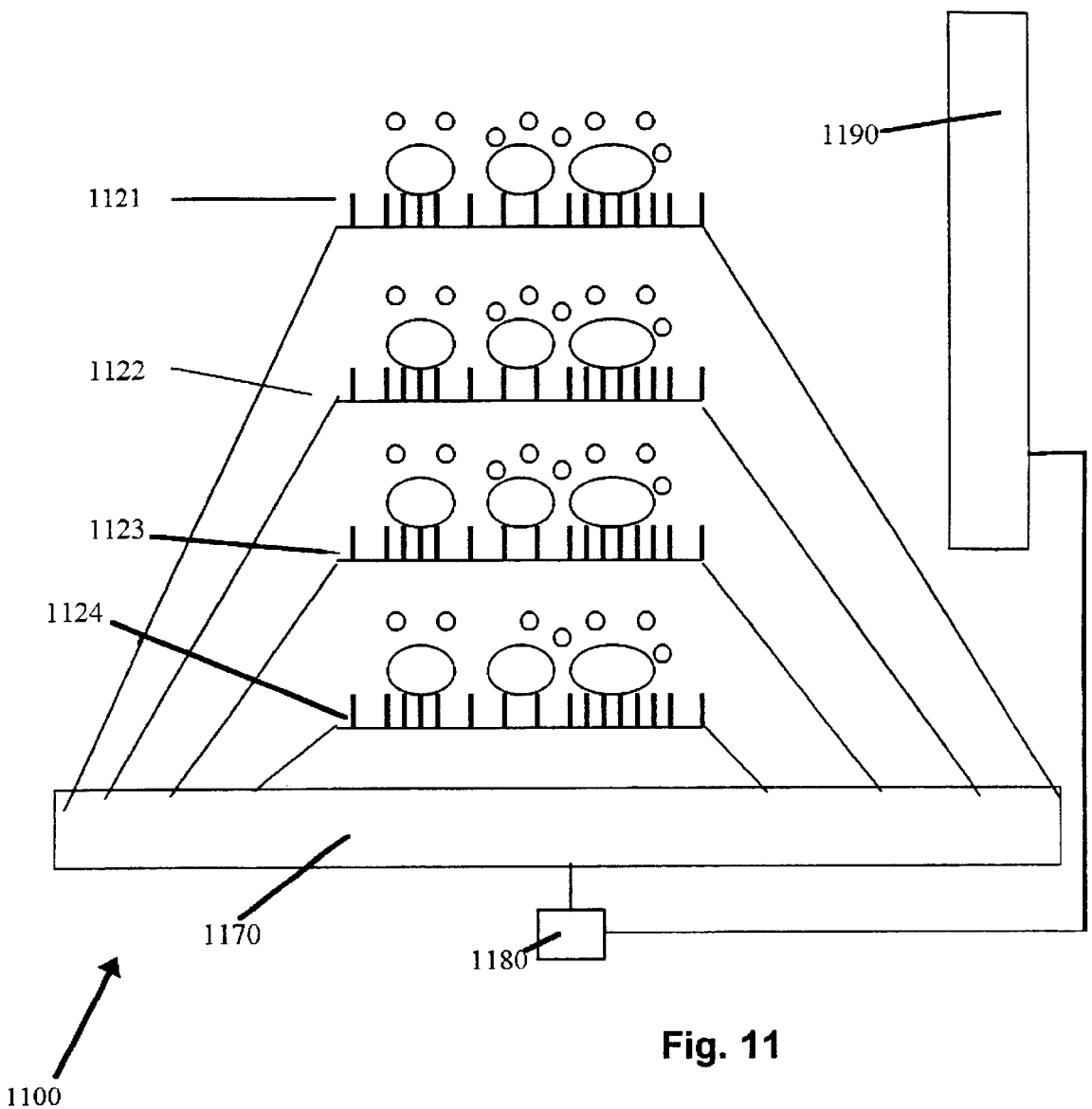
FIG. 11 is a schematic view of a sensor system for the detection/quantification of an analyte in which a serial dilution unit 1190 dilutes a sample and presents serial dilutions to multiple sensor strips 1121–1124.

The concentration of bacteria in milk is to be determined. A sample of milk is diluted from ten to one million fold in a serial dilution unit 1190 as shown in FIG. 11. Each dilution is applied to a separate sensor strip (sensor strips 1121–1124) that is prepared from aluminum foil, parahydroxybenzoic acid (the SAM), the enzyme lysozyme, and a packaging layer of NaCl and glucose. The sensitivity for a given strip is determined to be 3 cells per milliter for the present embodiment. A computer 1180 delivers portions of each serial dilution to independent sensor strips and then measures for an induced current in each strip. The increased induced current is measured in all samples from ten-fold to ten-thousand fold dilution. One hundred thousand-fold and one million-fold dilutions show no activity. The concentration of cells in the original milk sample is therefore calculated to be between 30,000 and 300,000 cells per milliliter (absolute strip sensitivity times levels of dilution). A finer serial dilution screen is performed in order to further narrow down the range of cell concentration values.

EXAMPLE 7

Figure 13:
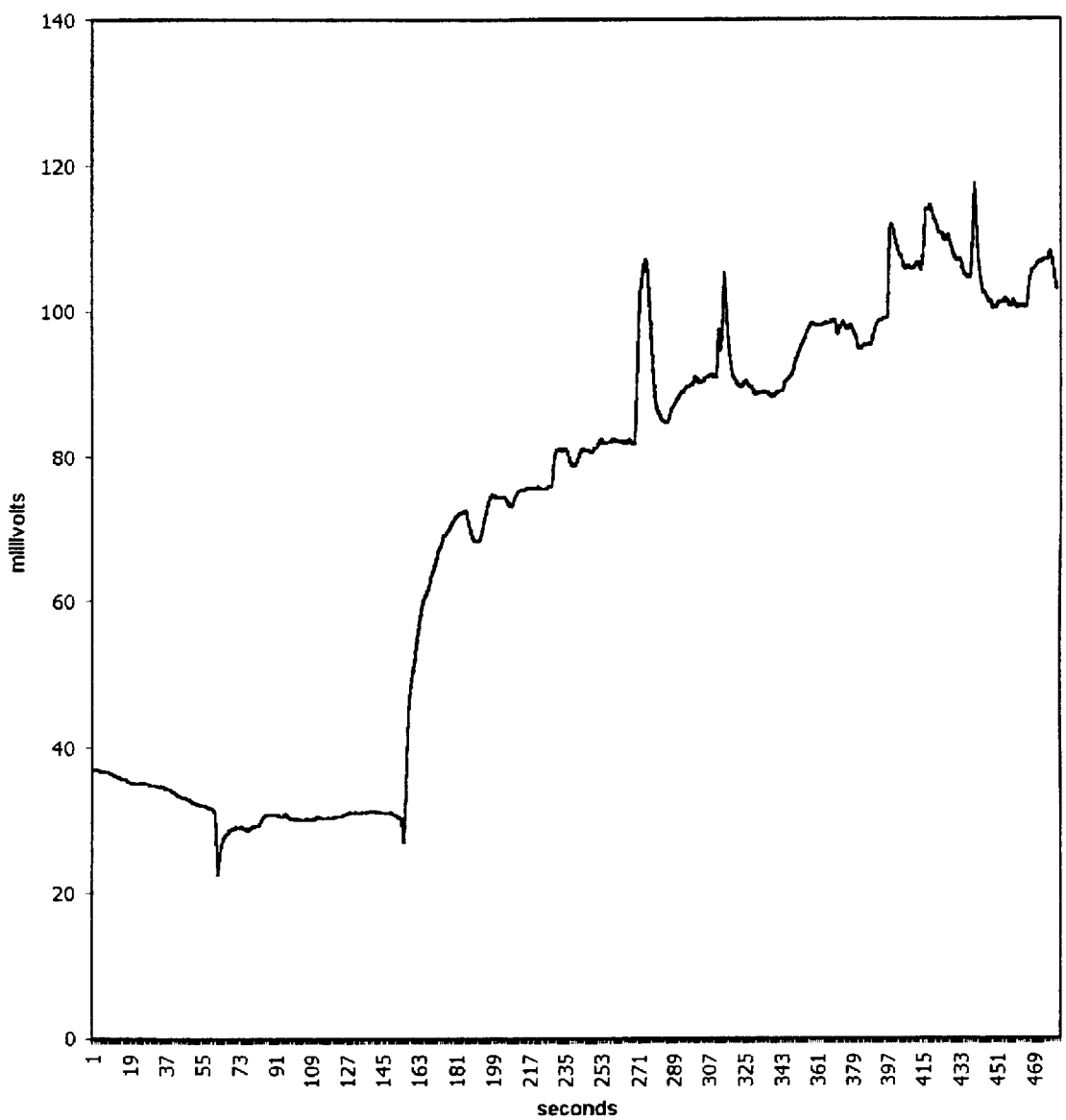
FIG. 13 is a graph of detection of lactose based on a sensor system embodiment described in FIG. 12.

1.5-milliliter plastic "Eppendorf" tubes were soaked in an aqueous solution of the lactose-hydrolyzing enzyme, lactase (beta-galactosidase). For the experiment, a detection unit was prepared that allowed for detection of magnetic flux by measurement of an induced electromotive force as per the sensor system embodiment of FIG. 12. Clean aluminum foil was contacted to an electrode of a commercially available digital multimeter. The foil was additionally contacted to a semiconductor-grade silicon chip that was coated with gold on one side, and this side was soldered to the second multimeter lead. Magnetic field flux impinging on the foil caused an induced emf to be produced in the foil. The foil was exposed to air for one minute, and then to an Eppendorf tube lacking lactase that contained goat milk. At approximately 2.5 minutes into the experiment, an Eppendorf tube that had been soaked in lactase and that also contained goat milk was placed in physical proximity to the aluminum foil in the detection unit. There was a significant increase in the induced emf (read in millivolts) due to the interaction of lactase with its substrates, water and milk-sugar, lactose. For this example, lactase enzyme molecules served as the macromolecules (not shown), while the Eppendorf tube served as the base unit of sensor element 1222, and the target analyte was lactose. The detection unit 1270 consisted of the multimeter, leads, foil, and semiconductor. The sensor element was composed of one Eppendorf tube and the physically absorbed lactase molecules. The data for the experiment are summarized in FIG. 13.

EXAMPLE 8

Figure 6:
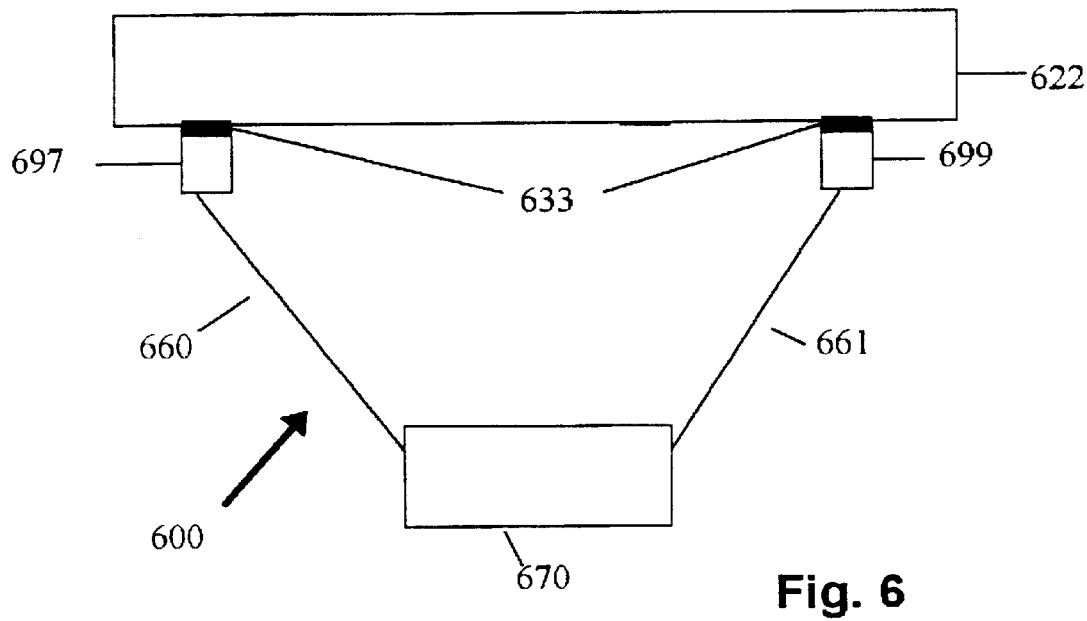
FIG. 6 is a schematic view of a fifth alternate embodiment of a sensor detection system 600 in accordance with the invention in which resistive elements 699 and 697 are incorporated into detector unit 670 leads 660 and 661. Adhesive agent 633 attaches each resistive element to one location on sensor strip 622.

A comparative clinical study was performed in order to determine the efficacy of the present invention in the detection of *Helicobacter pylori*, the causative agent of gastric ulcers and other gastrointestinal ailments. Single gastric biopsies were removed during gastrointestinal endoscopies. Biopsies were soaked in a buffered solution prepared for the detection of the enzyme urease. Urease is externally associated with *H. pylori* and its enzymatic degradation of urea can be linked to pH sensitive dyes in order to detect a color change if the enzyme (and by implication, the bacteria) is present Each biopsy was briefly removed from the urease detection solution, agitated in sterile saline in order to remove any associated *H. pylori* cells, and then returned to the urease detection solution. The saline solutions were then challenged with sensor strips according to the embodiment shown in FIG. 1, modified by the addition of resistive elements as shown in FIG. 6. The details of the sensor are aluminum foil (base member 120), parahydroxybenzoic acid SAM (130), antibodies specific for *H. pylori* (macromolecular layer 140), sodium chloride, and glucose (packaging layer 150). The strips were exposed to saline solutions and simultaneously contacted to leads (electrodes 160, 161) of a digital voltmeter (detection unit 170). Resistive elements 697 and 699 as shown in FIG. 6 were generally realized in the form of a layer of Scotch brand glue stick that aids in electrode-sensor strip contact while also serving the role of providing a resistive element between the strip and the leads. The glue thus served both as the adhesive agent 633 as well as the resistive elements 697, 699. The overall agreement between the present invention and the traditional urease test is currently 84% (Table I). Patient 32 was positive by the present invention in six different tests, all of which were complete within two minutes; the same patient was found positive by urease testing after 24 hours. It is believed that the sample contained a low concentration of *H. pyori*. The urease test is considered to be 90% accurate, with poor performance at low concentrations of cells. It may be noted that all disagreements between the results according to the present invention and the urease test reflect positive results detected by the present invention and negative results according to urease detection. In the case of patient 35, two strips of the present invention were read as positive while one was negative—a case for multiplexed systems based on the present invention.

TABLE 2

| Patient | Present Invention | Urease Test | Comment |
| --- | --- | --- | --- |
| 1 | Positive | Negative | Large Ulcer |
| 2 | Negative | Negative | Match |
| 3 | Negative | Negative | Match |
| 4 | Positive | Positive | Match |
| 5 | Negative | Negative | Match |
| 6 | Positive | Positive | Match |
| 7 | Positive | Negative | |
| 8 | Positive | Positive | Match |
| 9 | Negative | Negative | Match |
| 10 | Negative | Negative | Match |
| 11 | Positive | Negative | |
| 12 | Positive | Positive | Match |
| 13 | Positive | Negative | |
| 14 | Negative | Negative | Match |
| 15 | Negative | Negative | Match |
| 16 | Positive | Negative | |
| 17 | Positive | Positive | Match |
| 18 | Positive | Positive | Match |
| 19 | Negative | Negative | Match |
| 20 | Positive | Positive | Match |
| 21 | Negative | Negative | Match |
| 22 | Positive | Positive | Match |
| 23 | Positive | Positive | Match |
| 24 | Positive | Positive | Match |
| 25 | Positive | Positive | Match |
| 26 | Positive | Positive | Match |
| 27 | Negative | Negative | Match |
| 28 | Negative | Negative | Match |
| 29 | Negative | Negative | Match |
| 30 | Positive | Positive | Match |
| 31 | Positive | Positive | Match |
| 32 | Positive | Positive | Match (urease: 24 hours) |
| 33 | Positive | Positive | Match |
| 34 | Positive | Positive | Match |
| 35 | Positive | Positive | Match |
| 36 | Positive | Negative | |
| 37 | Positive | Positive | Match |
| 38 | Positive | Positive | Match |

While the sensing strip architecture of "base material-SAM-macromolecule" has been described previously, analyte detection and quantification based on electrical signals generated de novo in a sensor strip is believed to be new in the art. Prior-art sensors require applied electrical signals and generally rely on the chemical generation of charged species near the sensor surface. Today, there are neither aluminum foil-based sensor strips (as described in the Examples above) nor sensor strips designed exclusively for the detection of a de novo emf or current in a sensor strip. Thus, any sensor strip designed for the detection of a de novo electrical signal between two points of a sensor strip as a function of analyte presence would be produced and used with the express purpose of violating the invention described in this patent application. Such strips would find application in food pathogen detection, medical diagnostics, and the like, while the detection and serial dilution units would constitute separate components.

The present invention has been described with a certain degree of particularity, however those versed in the art will readily appreciate that various modifications and alterations may be carried out without departing from the spirit and scope of the following claims: Therefore, the embodiments and examples described here are in no means intended to limit the scope or spirit of the methodology and associated devices related to the present invention.

What is claimed is:

1. A sensor for detecting an analyte, comprising:
   a base member having a conductive electrical property;
   a macromolecular layer, wherein said macromolecular layer and said base member define a sensor strip, macromolecules of said macromolecular layer being interactive at a level of specificity with a predetermined analyte, wherein electrical current is generated responsive to presence of the analyte; and
   a semiconductive element situated between said base member and a detection unit that is connectable with said base member to establish a sensor circuit for detection of said electrical current.

2. The sensor according to claim 1, further comprising a chemical entity disposed between said base member and said macromolecular layer.

3. The sensor according to claim 1, further comprising two equipotential electrodes coupling said sensor strip to said detection unit.

4. The sensor according to claim 3 wherein said semiconductive element is physically associated with at least one of said electrodes.

5. The sensor according to claim 1, wherein said semiconductive element is physically associated with said sensor strip.

6. The sensor according to claim 1, wherein said semiconductive element is physically associated with the detection unit.

7. The sensor according to claim 1, wherein said base member is an electrically conducting foil.

8. The sensor according to claim 1 wherein said base member is an electrically conductive coating.

9. The sensor according to claim 1 wherein said base member is an electrically conductive thin film.

10. The sensor according to claim 1 wherein said base member is an electrically conductive ink.

11. The sensor according to claim 1 wherein said base member is an electrically conductive solid piece.

12. The sensor according to claim 1, wherein said base member is an electrically semiconducting foil.

13. The sensor according to claim 1, wherein said base member is an electrically semiconductive coating.

14. The sensor according to claim 1, wherein said base member is an electrically semiconductive thin-film.

15. The sensor according to claim 1, wherein said base member is an electrically semiconductive ink.

16. The sensor according to claim 1, wherein said base member is an electrically semiconductive solid piece.

17. The sensor according to claim 1, further comprising a packaging layer disposed above said macromolecular layer, said packaging layer being soluble in a medium that contains the analyte.

18. The sensor according to claim 1, wherein said sensor strip comprises a plurality of sensor strips.

19. A method for detecting a predetermined analyte, comprising the steps of:
   providing an electrically conductive base member;
   forming a macromolecular layer in proximity to said base member, wherein macromolecules of said macromolecular layer are interactive with said predetermined analyte, said base member and said macromolecular layer defining a sensor strip;
   exposing said predetermined analyte to said macromolecular layer;
   establishing a closed electrical circuit comprising said base member, a detection unit and at least one semiconductive element;
   detecting an electrical current generated in said electrical circuit, said current being responsive to presence of said predetermined analyte.

20. The method according to claim 19, further comprising the steps of:
   disposing a chemical entity proximate said base member; and
   forming said macromolecular layer proximate said chemical entity.

21. The method according to any of claim 19, wherein said step of detecting is performed by equipotentially coupling electrodes of said detection unit to said sensor strip.

22. The method according to claim 21, wherein said step of coupling is performed by passively contacting said electrodes to said sensor strip.

23. The method according to claim 21, wherein said semiconductive element is an organic semiconductor physically associated with one of said electrodes.

24. The method according to any of claim 19, wherein said semiconductive element is an organic semiconductor physically associated with said sensor strip.

25. The method according to any of claim 19, further comprising the step of disposing a packaging layer above said macromolecular layer, said packaging layer being soluble in a medium that contains said predetermined analyte.

26. The method according to claim 19, wherein said sensor strip comprises a plurality of sensor strips.

27. The method according to claim 19, further comprising the step of conducting said current to a device that is external to said sensor strip.

* * * * *